(12) United States Patent
Reo et al.

(10) Patent No.: US 10,517,650 B2
(45) Date of Patent: Dec. 31, 2019

(54) SPINAL STABILIZATION DEVICES, SYSTEMS, AND METHODS

(75) Inventors: Michael L. Reo, Redwood City, CA (US); Shigeru Tanaka, Half Moon Bay, CA (US)

(73) Assignee: Spinal Kinetics, Inc., Sunnyvale, CA (US)

( * ) Notice: Subject to any disclaimer, the term of this patent is extended or adjusted under 35 U.S.C. 154(b) by 1266 days.

(21) Appl. No.: 12/434,515

(22) Filed: May 1, 2009

(65) Prior Publication Data

US 2010/0280550 A1 Nov. 4, 2010

(51) Int. Cl.
*A61B 17/70* (2006.01)

(52) U.S. Cl.
CPC .............................. *A61B 17/7062* (2013.01)

(58) Field of Classification Search
CPC .......... A61F 2/4405; A61F 2002/30563; A61F 2002/4465; A61F 2002/30115; A61B 17/7062–17/707
USPC .... 606/246–249, 251–253; 623/17.11–17.16
See application file for complete search history.

(56) References Cited

U.S. PATENT DOCUMENTS

| | | | |
|---|---|---|---|
| 3,867,728 A | 2/1975 | Stubstad | |
| 4,932,969 A | 6/1990 | Frey et al. | |
| 5,071,437 A | 12/1991 | Steffee | |
| 5,171,281 A | 12/1992 | Parsons et al. | |
| 5,370,697 A | 12/1994 | Baumgartner | |
| 5,984,967 A * | 11/1999 | Zdeblick et al. | 623/17.16 |
| 6,063,121 A * | 5/2000 | Xavier et al. | 623/17.15 |
| 6,436,142 B1 * | 8/2002 | Paes et al. | 623/17.15 |
| 6,626,943 B2 | 9/2003 | Eberlin et al. | |
| 6,645,248 B2 | 11/2003 | Casutt | |
| 6,730,126 B2 * | 5/2004 | Boehm et al. | 623/17.15 |
| 6,733,532 B1 | 5/2004 | Gauchet et al. | |
| 7,402,176 B2 * | 7/2008 | Malek | 623/17.16 |
| 7,563,284 B2 | 7/2009 | Coppes et al. | |
| 7,909,875 B2 * | 3/2011 | Zielinski | 623/17.11 |
| 2005/0228500 A1 | 10/2005 | Kim et al. | |
| 2006/0058880 A1 * | 3/2006 | Wysocki et al. | 623/17.15 |
| 2006/0084988 A1 * | 4/2006 | Kim | 606/61 |
| 2006/0271044 A1 * | 11/2006 | Petrini et al. | 606/61 |
| 2007/0050033 A1 * | 3/2007 | Reo et al. | 623/17.12 |
| 2007/0055247 A1 | 3/2007 | Jahng | |
| 2007/0118225 A1 * | 5/2007 | Hestad et al. | 623/17.16 |
| 2007/0270952 A1 * | 11/2007 | Wistrom et al. | 623/17.11 |
| 2008/0077244 A1 * | 3/2008 | Robinson | 623/17.16 |
| 2008/0183209 A1 | 7/2008 | Robinson et al. | |
| 2009/0005873 A1 * | 1/2009 | Slivka et al. | 623/17.16 |

(Continued)

OTHER PUBLICATIONS

WO PCT/US2010/033311—Search Report, dated Jul. 9, 2010.

(Continued)

*Primary Examiner* — Jacqueline Johanas
(74) *Attorney, Agent, or Firm* — Haynes and Boone, LLP (57) ABSTRACT

This specification describes spinal stabilization devices that may be introduced into the spine via surgical procedures. In particular, this specification describes an inter-spinous process spacer having a core chosen, in one variation, to provide a kyphotic or lordotic angle to the device. The specification also describes systems including the described devices and methods of introducing the devices and systems into the spine to provide effective stabilization.

39 Claims, 5 Drawing Sheets

(56) References Cited

U.S. PATENT DOCUMENTS

2009/0076612 A1 3/2009 Reo
2009/0192616 A1* 7/2009 Zielinski .................... 623/17.16

OTHER PUBLICATIONS

U.S. Appl. No. 60/403,356, filed Aug. 15, 2002.
U.S. Appl. No. 60/403,402, filed Aug. 15, 2002.
Spinal Kinetics, Inc.'s Preliminary Invalidity Contentions (USDC, Case No. 5:09-cv-01201, *Synthes USA et al.* v. *Spinal Kinetics, Inc.,* Sep. 8, 2009).
Spinal Kinetics, Inc.'s Preliminary Invalidity Contentions—Exhibit 1 (chart comparing claims of U.S. Pat. No. 7,429,270 to Stubstad U.S. Pat. No. 3,867,728).
Spinal Kinetics, Inc.'s Preliminary Invalidity Contentions—Exhibit 2 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).
Spinal Kinetics, Inc.'s Preliminary Invalidity Contentions—Exhibit 3 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).
Spinal Kinetics, Inc.'s Preliminary Invalidity Contentions—Exhibit 4 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).
Spinal Kinetics, Inc.'s Preliminary Invalidity Contentions—Exhibit 5 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions—Exhibit 6 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).
Spinal Kinetics, Inc.'s Preliminary Invalidity Contentions—Exhibit 7 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).
Spinal Kinetics, Inc.'s Preliminary Invalidity Contentions—Exhibit 8 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Robert Hudgins, Georgia Inst. of Tech., Nov. 1998).
Spinal Kinetics, Inc.'s Preliminary Invalidity Contentions—Exhibit 9 (chart comparing claims of U.S. Pat. No. 7,429,270 to Stubstad U.S. Pat. No. 3,867,728 in view of Baumgartner U.S. Pat. No. 5,370,697).
Spinal Kinetics, Inc.'s Preliminary Invalidity Contentions—Exhibit 10 (chart comparing claims of U.S. Pat. No. 7,429,270 to Baumgartner U.S. Pat. No. 5,370,697 in view of Stubstad U.S. Pat. No. 3,867,728 and Steffe U.S. Pat. No. 4,071,437).
Spinal Kinetics, Inc.'s Preliminary Invalidity Contentions—Exhibit 11 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions—Exhibit 12 (chart comparing claims of U.S. Pat. No. 7,429,270 to Stubstad U.S. Pat. No. 3,867,728 in view of Development and Characterization of a Prosthetic Intervertebral Disc, Robert Hudgins, Georgia Inst. of Tech., Nov. 1998).
Spinal Kinetics, Inc.'s Preliminary Invalidity Contentions [Amended] (USDC, Case No. 5:09-cv-01201, *Synthes USA et al.* v. *Spinal Kinetics, Inc.,* Dec. 28, 2009).
Spinal Kinetics, Inc.'s Preliminary Invalidity Contentions [Amended]—Exhibit 1 (chart comparing claims of U.S. Pat. No. 7,429,270 to Stubstad U.S. Pat. No. 3,867,728).
Spinal Kinetics, Inc.'s Preliminary Invalidity Contentions [Amended]—Exhibit 2 (chart comparing claims of U.S. Pat. No. 7,429,270 to Coppes U.S. Pat. No. 7,563,284).
Spinal Kinetics, Inc.'s Preliminary Invalidity Contentions [Amended]—Exhibit 3 (chart comparing claims of U.S. Pat. No. 7,429,270 to Coppes U.S. Pat. No. 7,563,284 in combination with Stubstad U.S. Pat. No. 3,867,728).
Spinal Kinetics, Inc.'s Preliminary Invalidity Contentions [Amended]—Exhibit 4 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).
Spinal Kinetics, Inc.'s Preliminary Invalidity Contentions [Amended]—Exhibit 5 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).
Spinal Kinetics, Inc.'s Preliminary Invalidity Contentions [Amended]—Exhibit 6 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).
Spinal Kinetics, Inc.'s Preliminary Invalidity Contentions [Amended]—Exhibit 7 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions [Amended]—Exhibit 8 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).
Spinal Kinetics, Inc.'s Preliminary Invalidity Contentions [Amended]—Exhibit 9 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).
Spinal Kinetics, Inc.'s Preliminary Invalidity Contentions [Amended]—Exhibit 10 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Hudgins, Georgia Inst. of Tech., Nov. 1998).
Spinal Kinetics, Inc.'s Preliminary Invalidity Contentions [Amended]—Exhibit 11 (chart comparing claims of U.S. Pat. No. 7,429,270 to Stubstad U.S. Pat. No. 3,867,728 in view of Baumgartner U.S. Pat. No. 5,370,697).
Spinal Kinetics, Inc.'s Preliminary Invalidity Contentions [Amended]—Exhibit 12 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 4,071,437).
Spinal Kinetics, Inc.'s Preliminary Invalidity Contentions [Amended]—Exhibit 13 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions [Amended]—Exhibit 14 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions (USDC, Case No. 5:09-cv-01201, *Synthes USA et al.* v. *Spinal Kinetics, Inc.,* Sep. 30, 2010).
Spinal Kinetics, Inc.'s Second Amended Preliminary Invalidity Contentions—Exhibit 1 (chart comparing claims of U.S. Pat. No. 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 2 (chart comparing claims of U.S. Pat. No. 7,429,270 to Neuentwicklung eines lumbalen bewegungserhaltenden Bandscheibenimplantates, Feb. 25, 2002).
Spinal Kinetics, Inc.'s Second Amended Preliminary Invalidity Contentions—Exhibit 3 (chart comparing claims of U.S. Pat. No. 7,429,270 to Stubstad U.S. Pat. No. 3,867,728).
Spinal Kinetics, Inc.'s Second Amended Preliminary Invalidity Contentions—Exhibit 4 (chart comparing claims of U.S. Pat. No. 7,429,270 to Baumgartner PCT/CH2003/00247).
Spinal Kinetics, Inc.'s Second Amended Preliminary Invalidity Contentions—Exhibit 5 (chart comparing claims of U.S. Pat. No.

(56) References Cited

OTHER PUBLICATIONS 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 6 (chart comparing claims of U.S. Pat. No. 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 7 (chart comparing claims of U.S. Pat. No. 7,429,270 to Stubstad U.S. Pat. No. 3,867,728 in view of Eberlein U.S. Pat. No. 6,626,943).
Spinal Kinetics, Inc.'s Second Amended Preliminary Invalidity Contentions—Exhibit 8 (chart comparing claims of U.S. Pat. No. 7,429,270 to Stubstad U.S. Pat. No. 3,867,728 in view of Kim U.S. Pat. No. 7,153,325).
Spinal Kinetics, Inc.'s Second Amended Preliminary Invalidity Contentions—Exhibit 9 (chart comparing claims of U.S. Pat. No. 7,429,270 to Stubstad U.S. Pat. No. 3,867,728 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 10 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 11 (chart comparing claims of U.S. Pat. No. 7,429,270 to Coppes U.S. Pat. No. 7,563,284 to Stubstad U.S. Pat. No. 3,867,728).
Spinal Kinetics, Inc.'s Second Amended Preliminary Invalidity Contentions—Exhibit 12 (chart comparing claims of U.S. Pat. No. 7,429,270 to Coppes U.S. Pat. No. 7,563,284 in view of Eberlein U.S. Pat. No. 6,626,943).
Spinal Kinetics, Inc.'s Second Amended Preliminary Invalidity Contentions—Exhibit 13 (chart comparing claims of U.S. Pat. No. 7,429,270 to Coppes U.S. Pat. No. 7,563,284 in view of Kim U.S. Pat. No. 7,153,325).
Spinal Kinetics, Inc.'s Second Amended Preliminary Invalidity Contentions—Exhibit 14 (chart comparing claims of U.S. Pat. No. 7,429,270 to Coppes U.S. Pat. No. 7,563,284 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 15 (chart comparing claims of U.S. Pat. No. 7,429,270 to Coppes U.S. Pat. No. 7,563,284 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 16 (chart comparing claims of U.S. Pat. No. 7,429,270 to Baumgartner U.S. Pat. No. 5,370,697 in view of Stubstad U.S. Pat. No. 3,867,728).
Spinal Kinetics, Inc.'s Second Amended Preliminary Invalidity Contentions—Exhibit 17 (chart comparing claims of U.S. Pat. No. 7,429,270 to Baumgartner U.S. Pat. No. 5,370,697 in view of Eberlein U.S. Pat. No. 6,626,943).
Spinal Kinetics, Inc.'s Second Amended Preliminary Invalidity Contentions—Exhibit 18 (chart comparing claims of U.S. Pat. No. 7,429,270 to Baumgartner U.S. Pat. No. 5,370,697 in view of Kim U.S. Pat. No. 7,153,325).
Spinal Kinetics, Inc.'s Second Amended Preliminary Invalidity Contentions—Exhibit 19 (chart comparing claims of U.S. Pat. No. 7,429,270 to Baumgartner U.S. Pat. No. 5,370,697 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 20 (chart comparing claims of U.S. Pat. No. 7,429,270 to Baumgartner U.S. Pat. No. 5,370,697 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 21 (chart comparing claims of U.S. Pat. No. 7,429,270 to Gauchet U.S. Pat. No. 6,733,532 in view of Stubstad U.S. Pat. No. 3,867,728).
Spinal Kinetics, Inc.'s Second Amended Preliminary Invalidity Contentions—Exhibit 22 (chart comparing claims of U.S. Pat. No. 7,429,270 to Gauchet U.S. Pat. No. 6,733,532 in view of Eberlein U.S. Pat. No. 6,626,943).
Spinal Kinetics, Inc.'s Second Amended Preliminary Invalidity Contentions—Exhibit 23 (chart comparing claims of U.S. Pat. No. 7,429,270 to Gauchet U.S. Pat. No. 6,733,532 in view of Kim U.S. Pat. No. 7,153,325).
Spinal Kinetics, Inc.'s Second Amended Preliminary Invalidity Contentions—Exhibit 24 (chart comparing claims of U.S. Pat. No. 7,429,270 to Gauchet U.S. Pat. No. 6,733,532 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 25 (chart comparing claims of U.S. Pat. No. 7,429,270 to Gauchet U.S. Pat. No. 6,733,532 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 26 (chart comparing claims of U.S. Pat. No. 7,429,270 to Baumgartner U.S. Pat. No. 5,370,697 in view of Stubstad U.S. Pat. No. 3,867,728).
Spinal Kinetics, Inc.'s Second Amended Preliminary Invalidity Contentions—Exhibit 27 (chart comparing claims of U.S. Pat. No. 7,429,270 to Coppes U.S. Pat. No. 7,563,284 in view of Stubstad U.S. Pat. No. 3,867,728).
Spinal Kinetics, Inc.'s Second Amended Preliminary Invalidity Contentions—Exhibit 28 (chart comparing claims of U.S. Pat. No. 7,429,270 to Baumgartner U.S. Pat. No. 5,370,697 in view of Stubstad U.S. Pat. No. 3,867,728 in further view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 29 (chart comparing claims of U.S. Pat. No. 7,429,270 to Coppes U.S. Pat. No. 7,563,284 in view of Stubstad U.S. Pat. No. 3,867,728 further in view of Development and Characterization of a Prosthetic Intervertebral Disc, Hudgins, Georgia Inst. of Tech., Nov. 1998).
Burri et al., Neuentwicklung eines I mplantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002).
English Translation of Burri et al., Neuentwicklung eines I mplantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002), entitled Mechanical Engineering and Process Engineering at the Swiss Fedearl Institute of Technology Zurich (ETH Zurich) Feb. 2002.
Burri et al., Neuentwicklung eines lumbalen bewegungserhaltenden Bandscheibenimplantates, Feb. 25, 2002.
English Translation of Burri et al., Neuentwicklung eines lumbalen bewegungserhaltenden Bandscheibenimplantates, Feb. 25, 2002.
Hudgins, Development and Characterization of a Prosthetic Intervertebral Disc, Hudgins, Georgia Inst. of Tech., Nov. 1998.
Kweon et al., Optimal Design of Synthetic Intervertebral Disc Prosthesis Considering Nonlinear Mechanical Behavior, Dec. 20, 2001.

* cited by examiner

SPINAL STABILIZATION DEVICES, SYSTEMS, AND METHODS

This specification describes spinal stabilization devices that may be introduced into the spine via surgical procedures. In particular, this specification describes an inter-spinous process spacer having a core chosen, in one variation, to provide a kyphotic or lordotic angle to the device. The specification also describes systems including the described devices and methods of introducing the devices and systems into the spine to provide effective stabilization.

BACKGROUND

The spine is made up of twenty-four vertebrae that are stacked one upon the other to form the spinal column. The spine provides strength and support to allow the body to stand and to move with some flexibility. Each vertebra includes an opening through which the spinal cord passes. The collection of vertebrae thus protects the spinal cord. The spinal cord includes thirty-one pairs of nerve roots that branch from either side of the spinal cord off to other parts of the body. Those nerve roots extend through spaces between the vertebrae or in the vertebrae known as the neural foramen.

Between each pair of the adjacent vertebrae is an intervertebral disc. The disc is made up of three component structures: (1) the nucleus pulposus; (2) the annulus fibrosus; and (3) the vertebral endplates. The disc serves several purposes, including absorbing shock, relieving friction, and handling pressure exerted between the superior and inferior vertebral bodies associated with the disc. The disc also absorbs stress between the vertebral bodies, which stress would otherwise lead to degeneration or fracture of the vertebral bodies.

Disorders of the spine are some of the costliest and most debilitating health problems facing the populations of the United States and the rest of the world, costing billions of dollars each year. Moreover, as the population continues to age, the incidence of spinal disorders continues to grow, including those caused by disease, trauma, genetic disorders, and other causes.

Spine disorders are treated in a number of different ways. Medicinal treatments, exercise, and physical therapy are typical conservative treatment options. Less conservative treatment options include surgeries, such as microdiscectomy, kyphoplasty, laminectomy, dynamic stabilization, disc arthroplasty, and spinal fusion. Traditionally, these treatment options are used in isolation, rather than in combination, and the most conservative of the treatment options utilized to provide a desired result.

U.S. patent application Ser. No. 11/281,205, entitled "Prosthetic Intervertebral Discs," ("the '205 application"), was filed Nov. 15, 2005, was published as Publication 2007/0050033 on Mar. 1, 2007 and is assigned to Spinal Kinetics, Inc., the assignee of this application. The '205 application describes, inter alia, a treatment option that combines a prosthetic intervertebral disc with a dynamic stabilization system. The '205 application (and its provisional predecessor Ser. No. 60/713,671, filed Sep. 1, 2005) are incorporated by reference.

In 1992, Dr. Manohar Panjabi introduced a model of a dynamic spinal stabilization system that describes the interaction between structures that stabilize the spine and defined spinal instability as a region of laxity around the neutral resting position of a spinal segment, identified as the "neutral zone." Panjabi, M M., "The Stabilizing System of the Spine. Part II. Neutral Zone and Instability Hypothesis." J Spinal Disord 5 (4): 390-397, 1992b. There is some evidence that the breadth of the neutral zone increases as a result of intervertebral disc degeneration, spinal injury, and spinal fixation. Id. Panjabi has subsequently described dynamic stabilization systems that provide increased mechanical support in the neutral zone and decreased support away from the neutral zone. See, US Patent Publication No. 2004/0236329, dated Nov. 25, 2004, which is hereby incorporated by reference herein.

SUMMARY

The present invention, spinal stabilization components, systems, and methods for their use. The spinal stabilization components—in particular, inter-spinous process spacers—are suitable for use in isolation, with other spinal stabilization components, with one or more replacement disc components, with one or more replacement disc nucleus components, and in other systems.

Other spinal stabilization devices are used for facet joint augmentation and replacement, facet joint implants, lateral spinal stabilization devices, anterior spinal stabilization devices, and the like. One variation of a system containing an inter-spinous stabilization member comprises a combination with one or more pedicle-based stabilization members such as those functioning by biasing a pair of adjacent vertebral bodies apart. The combined action of the inter-spinous spacer and the pedicle based members creates a moment arm that relieves pressure from the disc.

Specifically, a dynamic stabilization device is comprised of a posterior spacer member located between a pair of spinous processes on adjacent vertebral bodies and provides a combination of stabilizing forces to one or more spinal units to assist in bearing spinal loads, whether in compression, tension, or torsion, and in transferring or sharing those loads between vertebrae. The posterior spacer maintains spacing between the pair of adjacent vertebral bodies while allowing their relative motion.

The posterior spacer includes a generally compliant, compressible, elastic material core situated within the device in a position that is not collinear with the localized spinal axis. The core may have: a.) a circular cross-section and be cylindrical, tapering, barrel-shaped, etc., b.) an oval cross section and be cylindrical, tapering, barrel-shaped, etc., or c.) a square, rectangular, or other trapezoidal cross-section. The tapering cores may provide a lordotic or kyphotic angle, as desired. The core may be supported by upper and lower support structures having concave shapes adjacent the core that generally correspond to the shape of the adjacent compliant core. The upper and lower support structures may be configured to attach directly to the spinous processes and may be configured to attach to fixing structures that in turn fixedly attach directly to the spinous processes.

The device may further comprise at least one fiber that associates the movement of the upper and lower support structures, e.g., by passage of that fiber (or fibers) between the upper and lower support structures. That relationship created by the fiber or fibers may be the result of any of a number of structural features. For instance, the fiber or fibers may be wound through openings, e.g., circular openings, oval openings, slots, etc., generally placed in the upper and lower support structures laterally to the core. The device may comprise one or more fibers wound in single layers or multiple layers. The fibers themselves may be monofilament or multifilament. In another variation, one or more ribbons associating the upper and lower support structures may be used.

The device may be configured in a number of different ways for introduction into the inter-spinous-process space. The device may be configured for introduction into the inter-spinous-process space as an assembled structure. The device may be configured such that the core in isolation is assembled into the remainder of the device after the coreless device has been introduced into the inter-spinous-process space. The device may be configured such that the core and the support structures are assembled into two previously sited fixing structures. The device may be configured such that the core, perhaps conical or tapered in shape, adjusts spacing or taper between the two adjacent vertebrae during placement of the device. These devices may be introduced to the spine using posterior or lateral approaches or a combination of the two.

The spacer device itself may take other shapes or forms, however, depending upon the size and shape of the spinal treatment site and may be configured for post-operative adjustment of height or angle relative to the core and support structures together or individually and may engage spinal structures in a number of orientations or configurations to achieve the desired physiological result as described herein.

The device components may be formed from known materials suitable for physiological implants and support structures. As noted elsewhere, the core may comprise an elastic, compliant material or materials, e.g., a polyurethane, polysiloxane ("Silicone"), or an appropriate elastomer. The upper and lower support members and the attachment structures may be formed of suitably stiff materials, e.g., stainless steels, superelastic alloys such as nitinol, titanium and titanium alloys, cobalt-chromium, polymeric materials such as polycarbonates, PEEK, or an appropriate engineering polymers.

Finally, the invention includes systems comprising our inter-spinous process spacer and an prosthetic intervertebral disc or dynamic stabilizing devices to obtain desired therapeutic results.

BRIEF DESCRIPTION OF THE FIGURES

The Figures are not necessarily drawn to scale. Some components and features have been exaggerated for clarity.

DESCRIPTION

Figure 1:
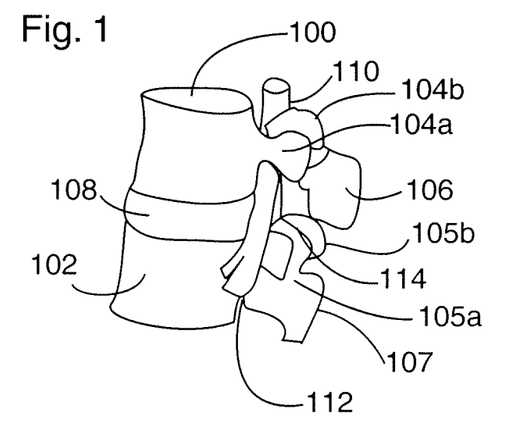
FIG. 1 is a lateral view of a pair of adjacent vertebral bodies, including representation of the foramen and nerve roots traversing the foramen, the intervertebral disc, the spinous processes, etc.

FIG. 1 illustrates a pair of adjacent vertebrae, including a superior or upper vertebral body (100) and an inferior or lower vertebral body (102). Upper vertebral body (100) includes a pair of transverse processes (104a, 104b) and a spinous process (106) extending generally posteriorly. Lower vertebral body (102) includes a pair of transverse processes (105a, 105b) and a spinous process (107). A disc (108) is located between the superior vertebral body (100) and the inferior vertebral body (102). The spinal cord (110) extends through a central passage formed by the spinal column, and nerve roots (112) transverse the foramenal space (114) defined by the pair of vertebral bodies.

When the disc is damaged due to trauma, disease, or other disorder, the superior vertebral body (100) and inferior vertebral body (102) tend to collapse upon each other, thereby decreasing the amount of space formed by the foramen (114). This result also commonly occurs when the vertebral bodies are afflicted with disease or are fractured or otherwise damaged. When the foramenal space is decreased, the vertebral bodies (100, 102) may impinge upon the nerve root (112), causing discomfort, pain, and possible damage to the nerve root. The inter-spinous process spacers described herein are intended to alleviate this problem by maintaining or restoring the spacing between the adjacent vertebrae and protect the nerve root from impingement by those vertebrae.

Figure 2:
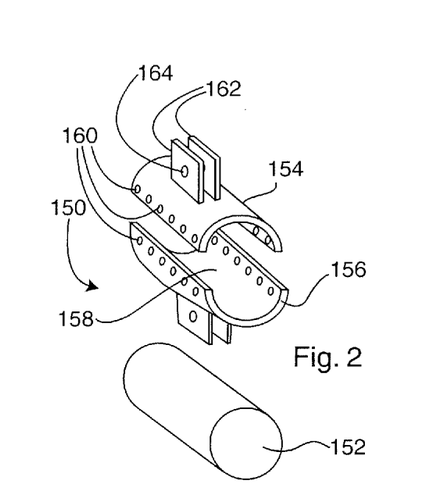
FIG. 2 is an exploded view of a variation of the inter-spinous process spacers.

FIG. 2 shows a partially exploded, perspective view of one variation of an inter spinous process spacer (150). This variation includes a core (152) that is generally cylindrical in shape and formed of a resilient, compliant, elastic material. The core member (152) may comprise a hydrogel, gel, elastomer, polyurethane, or other polymeric material suitable for providing the shock absorbing and spacing functions necessary to stabilize the intervertebral joint.

Examples of suitable block copolymer type thermoplastic elastomers (TPE) products include STYROFLEX (BASF), KRATON (Shell chemicals) styrene-butadiene-styrene block copolymer, PELLETHANE (Dow chemical), PEBAX, ARNITEL (DSM), and HYTREL (Du Pont). Alloy-type TPE's such as SANTOPRENE (Monsanto), GEOLAST (Monsanto), and ALCRYN (Du Pont) as well as TPE's such as metallocene-catalyzed polyolefin plastomers and elastomers and reactor-made thermoplastic polyolefin elastomers are also suitable.

Of special interest are the polycarbonate-polyurethane and silicone-urethane TPE's.

In the variation shown in FIG. 2, the device (150) includes an upper end plate (154) and a lower end plate (156). In some variations discussed elsewhere, the end plates (154, 156) are split into two components for ease of placement: a support structure for cradling the core (152) and a fixing structure for attachment to the spinous process of the vertebra.

However, in this variation, each of the end plates (154, 156) includes a concave opening or area (158) that substantially conforms in shape to the core (152). Also seen in this variation are a number of openings (160) used for the filaments (not shown in this drawing, but see 200 in FIG. 9) that contribute (with the core (152)) to associating the movement of the upper end plate (154) with that of the lower end plate (156).

Figure 12:
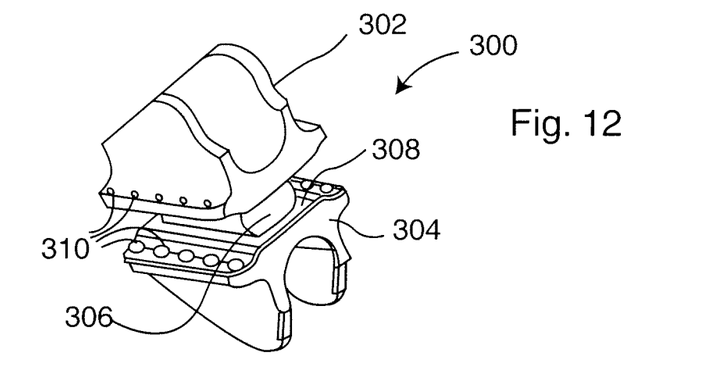
FIG. 12 provides a perspective views of a molded variation of the inter-spinous process spacers.

Each of the end plates (154, 156) includes a pair of tabs (162) that, in turn, include openings (164) for affixing the device (150) to a spinous process. As should be apparent, but in any case is shown in FIG. 12, the extended spinous process fits between the two tabs (162). The openings (164) may be used in conjunction with bone screws, pins, adhesives, filaments or cordage, etc. as fixing devices.

The specific sizes of the end plates (154, 156) are chosen with at least two criteria in mind: comparatively larger devices (and endplates) are introduced into lumbar region intervertebral spaces than the comparatively smaller devices introduced into the cervical region intervertebral spaces and the end plates, after implantation of the device, must not interfere with each other during spinal flexing. As a practical matter, if a device such as shown in FIG. 2 has a substantially circular cross-section, the gap at each side of the device allowing such freedom from interference may be 15° or more on each side of the circular cross-section.

The end plates (154, 156) shown in FIG. 2, as well as any of the other components shown here (other than the core and the filaments, sheets, and membranes) may comprise one or more of the following physiologically acceptable materials having appropriate mechanical properties: titanium, titanium alloys, stainless steel, cobalt/chromium, polymers such as ultra high molecular weight polyethylene (UHMW-PE), polyether ether ketone (PEEK), etc.; ceramics; graphite; etc. The tabs (162) on the endplates (154, 156) may be treated in various ways to encourage bone growth, e.g., by roughening the surface or spraying metallic granular titanium onto the surface of the tabs (162)—at least where the tabs comprise a titanium or titanium alloy. Certain calcium phosphate treatments may encourage bone growth as well.

This spacer design, having openings (160) for the fibers at the periphery of the end plates (154, 156), allows the physician a great deal of flexibility in selecting a core (e.g., 152)—with a particular shape or size to remedy problems with a particular patient's anatomy or to remedy a disease. The end plates may first be affixed to the spinous processes without a core but (perhaps) with the filaments loosely in place. A core "trial"—an instrument (or collection of instruments) used to select an appropriately sized core by introducing a number of core-substitutes into the empty inter spinous process spacer until a desired result is achieved, e.g., appropriate height or appropriate intervertebral angle—may be used to select the optimum core. The filaments may then be pulled tight and the core captured in the device. Fixing the free ends of the filaments may be by tying or other similar method.

Figure 3:
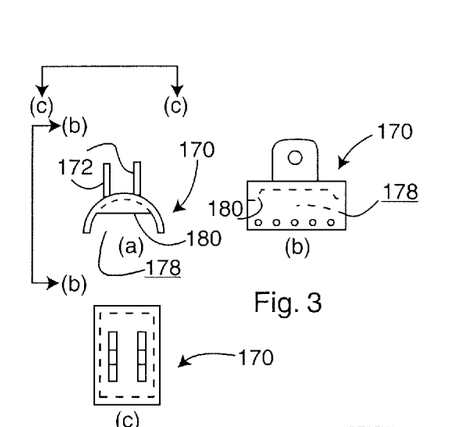
FIG. 3 provides three views of one of the support structures of the inter-spinous process spacers.

FIG. 3 shows three views (end, side, and top views) of another variation of our integrated end plate (170) also having tabs (172) for affixing the end plate (170) to the spinous process. The end plate (170) has a cavity (178) that substantially conforms to the shape of the core that will be inserted there. This variation includes a pair of stops (180) that tend to maintain the core in an appropriate site in the completely assembled device.

Figures 4, 5:
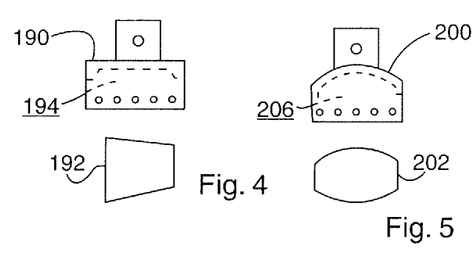
FIGS. 4-8 provide side views of several variations of our inter-spinous process spacers.

FIG. 4 shows a single end plate (190) and its corresponding core member (192). The core (192) is tapered and engages with the cavity (194) in the endplate (190). This relationship may provide a non-angular relationship between the two adjacent vertebrae.

FIG. 5 shows an end plate (200) and a core (202). The core (202) is barrel-shaped and the endplate (200) has a cavity (206) corresponding to the core (202) shape.

Figures 6, 7:
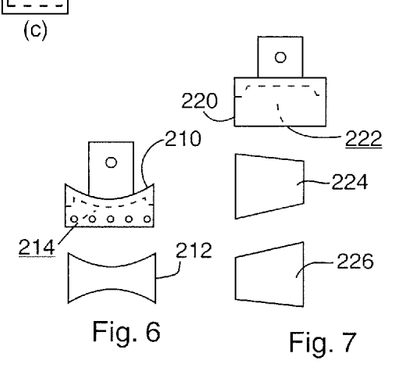

FIG. 6 shows an end plate (210) and a core (212) from still another variation of our inter spinous process spacer. In this instance, the core (212) has a curved thimble shape corresponding to the cavity (214) in that end plate.

FIG. 7 shows an end plate (220) having a generally symmetric shape in its cavity (214). Two cores (224, 226) are shown as alternatives to provide a kyphotic or lordotic angle to the device.

Figure 8:
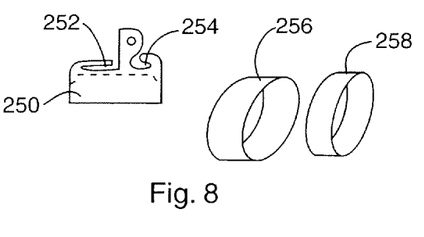
Figure 9:
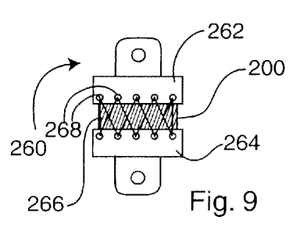
FIG. 9 is a side view of a variation of the inter-spinous process spacer depicting one placement of fibers between upper and lower support structures.

FIGS. 8 and 9 show two alternatives in associating the movement of the upper and lower end plates.

FIG. 8 shows an end plate (250) having a pair of open-ended slots (252, 254) into which specifically sized ribbons (256, 258) may be placed to hold the assembled device with its pair of end plates (250) and core in position.

FIG. 9 shows an assembled device (260) having an upper end plate (262), a lower end plate (264), and a core (266). Also shown in FIG. 9 are filaments (200) that pass through openings (268) in each of the end plates (262, 264) and, after implantation, influence the movements of the two end plates (262, 264).

The movement of one vertebral body with respect to an adjacent vertebral body is quite complex. Movement of a lower vertebral body with respect to an upper vertebral body in flexion, in extension, laterally, and twisted about its axis is not a circular rotation or linear movement. The effects of the positioning (or geometry) of the facet joints with respect to the intervertebral disc, their respective compressibilities, and other related anatomical features all mandate a responsive motion of the upper vertebral body that is quite complex.

Additionally, the adjacent intervertebral disc has a measure of compressibility. The value for a healthy natural cervical disc is 737 N/mm+/−885 N/mm.

The responsive motions in flexion, extension, and lateral flexion are generally rotational in nature. However, each such rotation includes a moving or instantaneous center or axis of rotation. The viscous and elastic nature of the disc and varying effect of the facet joints on the vertebral body movement contributes to this complexity. Our prosthetic inter-spinous process device, whether used in isolation or when used in conjunction with a prosthetic intervertebral disc such as shown in U.S. Pat. No. 7,153,325, contribute to the natural movement of the spinal joint in response to external forces or moments. In the implant described herein, the specific responsive movements are due to the choice of materials, their compositions, certain of their physical parameters (compressibility, the disclosed geometry, etc.), and, in some cases, the manner in which the core is attached to the assembly.

Figure 10:
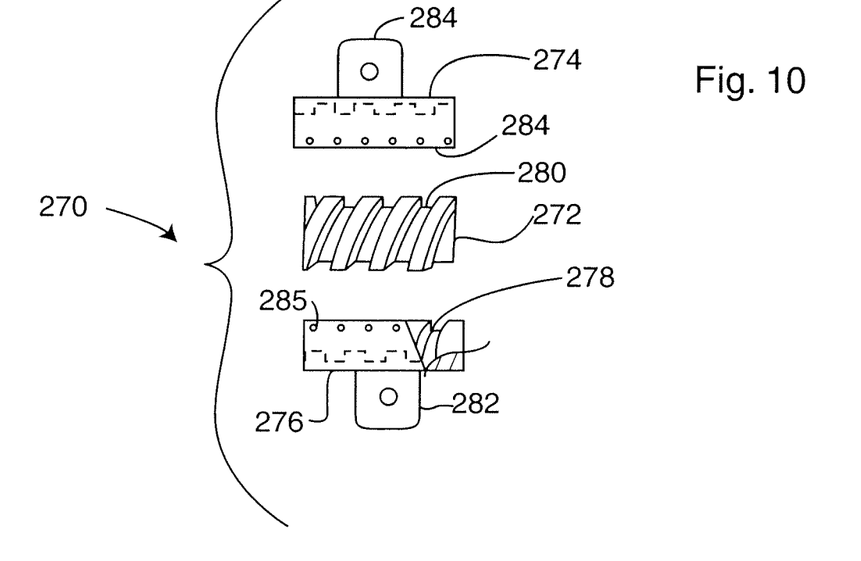
FIG. 10 is a side view, partial cutaway, exploded view of a variation of the inter-spinous process spacer having a threaded, constant diameter core.

FIG. 10 is a side view, partial cutaway, exploded view of a variation (270) of our inter-spinous process spacer having a threaded, constant diameter core (272). The variation includes an upper end plate (274) and a lower end plate (276) having cooperating grooves (278) in each end plate (272, 274) that match grooves (280) in the core (272). The core (272) may be screwed into the upper end plate (274) and the lower end plate (276) after the end plates are introduced into the space between the adjacent inter-spinous processes. The end plates (272, 274) include attachment structures (282, 284) having a support function as well. A filament or filaments may be passed through the openings (285) as discussed with regard to other variations.

Figure 11:
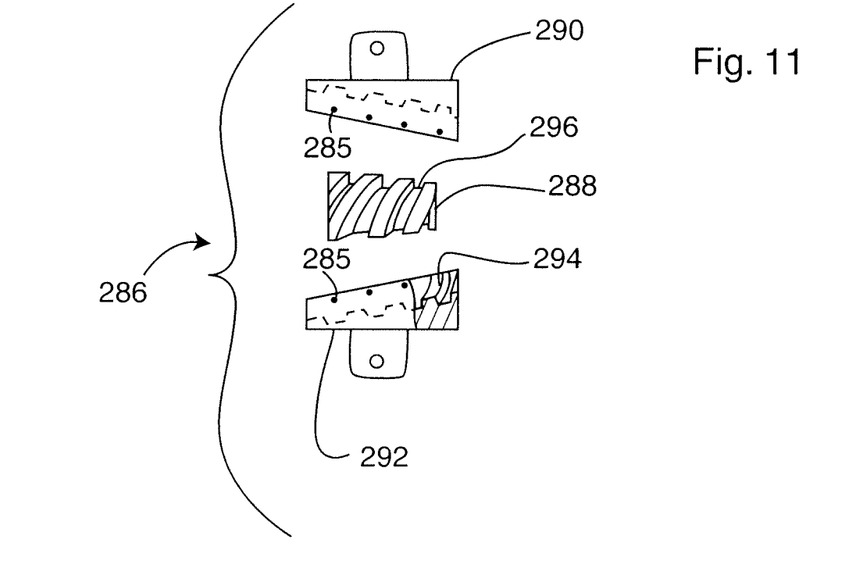
FIG. 11 is a side view, partial cutaway, exploded view of a variation of the inter-spinous process spacer having a threaded, tapered core.

FIG. 11 is a side view, partial cutaway, exploded view of a variation (286) of our inter-spinous process spacer having a threaded, tapered core (288). The variation includes an upper end plate (290) and a lower end plate (292) having cooperating grooves (294) in each end plate (286, 288) that match grooves (296) in the core (288). The core (288) may be screwed into the upper end plate (290) and the lower end plate (292) after the end plates are introduced into the space between the adjacent inter-spinous processes. Since the core (288) is tapered, this feature may be used to change the spacing between the upper end plate (290) and the lower end plate (292). A filament or filaments may be passed through the openings (285) as discussed with regard to other variations.

FIG. 12 shows a variation (300) of our device, without fibers for clarity, comprising an upper end plate (302) and a lower end plate (304). The core (306) rests in a cavity (308), the shape of which conforms to the shape of the core (306). The openings (310) for filaments are situated farther than the axis of the core (306) than are the devices described elsewhere. The wider hole (310) spacing provides a significantly different geometry for between the end plates (302, 304). The movement of one end plate affects the movement of the other with a controlled interaction and consequently causes a controlled reaction between the adjacent spinous processes.

Figure 13:
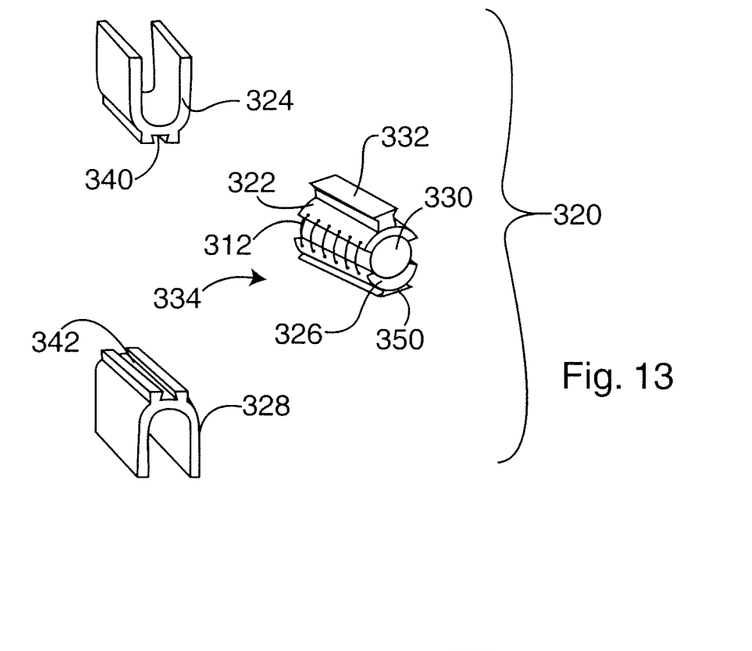
FIG. 13 is a perspective, partially exploded view of a variation of the inter-spinous process spacer in which the core is installed after the fixation members are joined to the spinous processes.

FIG. 13 shows an exploded perspective view of a variation of our device (320) where the upper end plate is made up of a support structure (322) and a fixation structure (324) for affixing the device to an upper spinous process. Similarly, the functional lower end plate is made up of a support structure (326) and a fixation structure (328) for affixing the device to a just lower spinous process. In FIG. 13, the upper support structure (322) and the lower support structure (326) surround a core (330) that is assembled with one or more filaments (332) forming a central core assembly (334). The central core assembly (334) is shown to have longitudinal sliding dovetails (336, 338) that slide into matching keyways (340, 342) in the upper fixation structure (324) and the lower fixation structure (328).

Simply, during implantation, upper fixation structure (324) and lower fixation structure (328) may be affixed to spinous processes on adjacent vertebrae and, after determining the proper size, angle, etc. of the central core assembly (334), the longitudinal sliding dovetails (336, 338) of the chosen core assembly (334) is introduced posteriorly into the matching keyways (340, 342) in the upper fixation structure (324) and the lower fixation structure (328).

The mating or cooperating dovetails and keyways may be configured in various of the components so that the core assembly is made to enter the fixation structures laterally or at an angle posterio-laterally.

Figure 14:
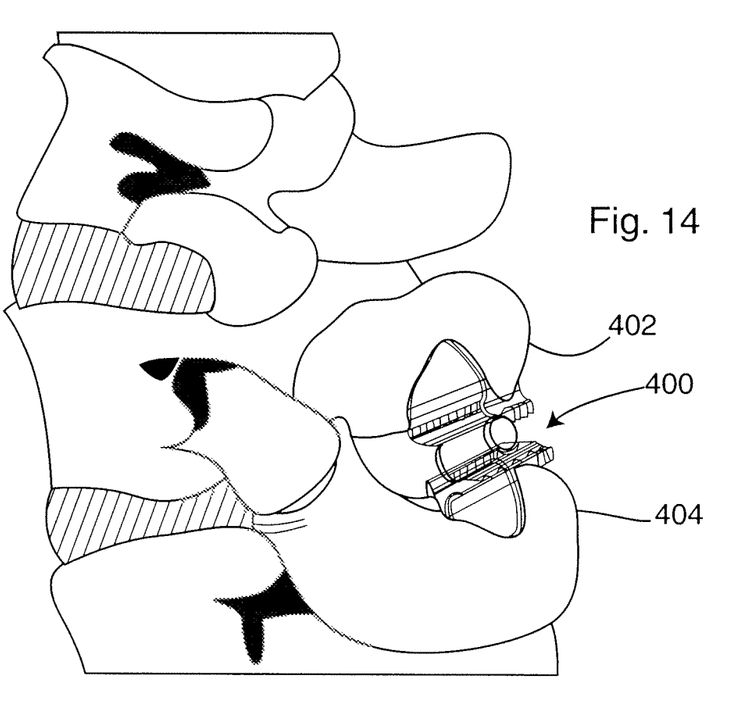
FIG. 14 provides a perspective view of a variation of the inter-spinous process spacer after placement between adjacent spinous processes.

Finally, FIG. 14 depicts our inter spinous process spacer (400) after implantation in a spine, specifically between an upper spinous process (402) and a lower spinous process (404).

As noted above, U.S. patent application Ser. No. 11/281,205, entitled "Prosthetic Intervertebral Discs," ("the '205 application"), was filed Nov. 15, 2005, was published as Publication 2007/0050033 on Mar. 1, 2007 and is assigned to Spinal Kinetics, Inc., the assignee of this application. The '205 application describes, inter alia, a treatment option that combines a prosthetic intervertebral disc with a dynamic stabilization system. The '205 application (and its provisional predecessor Ser. No. 60/713,671, filed Sep. 1, 2005) are incorporated by reference. Our inter spinous process spacer is also suitable for use in combination with the prosthetic intervertebral discs such as those described in U.S. patent application Ser. No. 10/903,276, filed Jul. 30, 2004, ("the '276 application"), published as Publication 2005/0228500 on Oct. 13, 2005, which is also incorporated by reference herein.

Conventions

This description is not limited to the specifically described variations. It is also to be understood that the terminology used is solely for the purpose of describing particulars of the devices and methods. The terminology is not limited and the scope of the present invention is limited only by the appended claims.

Where a range of values is provided, the description specifically includes each intervening value, to at least the tenth of the unit of the lower range limit unless the context clearly dictates otherwise, found between the upper and lower range limits of that range and any other stated or intervening value in that stated range.

Unless defined otherwise, all technical and scientific terms have the same meaning as commonly understood by one of ordinary skill in the art to which the described device and methods belong. All publications mentioned herein are incorporated herein by reference for the purpose of disclosing and describing the methods and/or materials in connection with which the publications are cited.

Singular forms "a", "an," and "the" include plural referents unless the context clearly dictates otherwise.

As will be apparent to those of skill in the art upon reading this disclosure, each of the described device and method has discrete components and features that may be readily separated from or combined with the features of any of the other several devices and methods.

It is to be understood that the described devices and processes that are the subject of this patent application are not limited to the particular described variations, as such may, of course, vary. In particular, our description is meant to include implanted or implantable combinations of two or more of the specific devices described herein, to the extent that the devices are compatible with one another.

We claim as our invention:

1. An interspinous process spinal stabilization device implantable between upper and lower spinous processes of adjacent vertebrae in a spine, the spine having a spinal axis that is substantially parallel with the spinal cord in the spine, the device comprising:
   a.) an upper end plate configured to attach to an upper spinous process with a first fixation structure, and further configured with a cavity situated opposite from the first fixation structure, the cavity substantially conforming in shape to a compressible, elastic, polymeric core member,
   b.) a lower end plate configured to attach to a lower spinous process with a second fixation structure, and further configured with a cavity situated opposite from the second fixation structure, the cavity substantially conforming in shape to the compressible, elastic, polymeric core member,
   c.) one or more flexible members selected from the group consisting of fibers, ribbons, and membranes extending between the upper end plate and the lower end plate and associating movement in one end plate with movement in the other end plate, and
   d.) said compressible, elastic, polymeric core member having a core axis along a core length, the core member having dimensions perpendicular to the core length that are all shorter than the core length, the core axis forming an included angle with the spinal axis greater than about 35° to and including 90°.

2. The device of claim 1 wherein the core member has a core cross-section perpendicular to the core axis and wherein the core cross-section has a shape selected from the group consisting of substantially circular, oval, square, rectangular, and polygonal.

3. The device of claim 1 wherein the core member has a core cross-section perpendicular to the core axis and wherein the core cross-section is substantially circular.

4. The device of claim 1 wherein the core member comprises elastomeric material.

5. The device of claim 1 wherein the core member comprises TPE.

6. The device of claim 2 wherein the core member is tapered.

7. The device of claim 3 wherein the core member is tapered.

8. The device of claim 2 wherein the core member is threaded.

9. The device of claim 7 wherein the core member is threaded.

10. The device of claim 1 wherein the upper end plate comprises the first fixation structure and an upper support member,
wherein the upper support member contains the cavity substantially conforming in shape to the core member, and
wherein the first fixation structure and the upper support member are removably slidably attachable to each other, and
wherein the lower end plate comprises the second fixation structure and a lower support member,
wherein the lower support member contains the cavity substantially conforming in shape to the core member, and
wherein the second fixation structure and the lower support member are removably slidably attachable to each other.

11. The device of claim 10 wherein the first and second fixation structures comprise slidable keyways and wherein the upper and lower support members comprise members slidable within the slidable keyways.

12. The device of claim 1 wherein the one or more flexible members comprise more than one fiber interconnecting upper and lower end plates.

13. The device of claim 1 wherein the one or more flexible members comprise more than one ribbon interconnecting upper and lower end plates.

14. A spinal stabilization system comprising the interspinous process spinal stabilization device of claim 1 and an implantable prosthetic disc.

15. An interspinous process spinal stabilization device implantable between upper and lower spinous processes of adjacent vertebrae in a spine, the spine having a spinal axis that is substantially parallel with the spinal cord in the spine, the device comprising:
 a.) an upper end plate configured to attach to an upper spinous process with a first fixation structure comprising a pair of tabs configured such that, when the device is implanted, the upper spinous process lies between the pair of tabs, and further configured with a cavity situated opposite from the first fixation structure, the cavity substantially conforming in shape to a compressible, elastic, polymeric core member,
 b.) a lower end plate configured to attach to a lower spinous process with a second fixation structure comprising a pair of tabs configured such that, when the device is implanted, the lower spinous process lies between the pair of tabs, and further configured with a cavity situated opposite from the second fixation structure, the cavity substantially conforming in shape to the compressible, elastic, polymeric core member,
 c.) one or more flexible members selected from the group consisting of fibers, ribbons, and membranes extending between the upper end plate and the lower end plate and associating movement in one end plate with movement in the other end plate, and
 d.) said compressible, elastic, polymeric core member having a core axis along a core length, the core member having dimensions perpendicular to the core length that are all shorter than the core length, the core axis forming an included angle with the spinal axis greater than about 35° to and including 90°.

16. The device of claim 15 wherein the core member has a core cross-section perpendicular to the core axis and wherein the core cross-section has a shape selected from the group consisting of substantially circular, oval, square, rectangular, and polygonal.

17. The device of claim 15 wherein the core member has a core cross-section perpendicular to the core axis and wherein the core cross-section is substantially circular.

18. The device of claim 15 wherein the core member comprises elastomeric material.

19. The device of claim 15 wherein the core member comprises TPE.

20. The device of claim 16 wherein the core member is tapered.

21. The device of claim 17 wherein the core member is tapered.

22. The device of claim 16 wherein the core member is threaded.

23. The device of claim 21 wherein the core member is threaded.

24. The device of claim 15 wherein the upper end plate comprises the first fixation structure and an upper support member,
wherein the upper support member contains the cavity substantially conforming in shape to the core member, and
wherein the first fixation structure and the upper support member are removably slidably attachable to each other, and
wherein the lower end plate comprises the second fixation structure and a lower support member,
wherein the lower support member contains the cavity substantially conforming in shape to the core member, and
wherein the second fixation structure and the lower support member are removably slidably attachable to each other.

25. The device of claim 24 wherein the first and second fixation structures comprise slidable keyways and wherein the upper and lower support members comprise members slidable within the slidable keyways.

26. The device of claim 15 wherein the one or more flexible members comprise more than one fiber interconnecting upper and lower end plates.

27. The device of claim 15 wherein the one or more flexible members comprise more than one ribbon interconnecting upper and lower end plates.

28. The device of claim 15 wherein the tabs contain openings for fixation to the upper and lower spinous processes.

29. A spinal stabilization system comprising the interspinous process spinal stabilization device of claim 15 and an implantable prosthetic disc.

30. An interspinous process spinal stabilization device implantable between upper and lower spinous processes of adjacent vertebrae in a spine, the spine having a spinal axis that is substantially parallel with the spinal cord in the spine, the device comprising:
- a.) an upper end plate configured to attach to an upper spinous process with a first fixation structure comprising a pair of tabs configured such that, when the device is implanted, the upper spinous process lies between the pair of tabs, each of the tabs containing openings for fixation to the upper spinous process, and further configured with a cavity situated opposite from the first fixation structure, the cavity substantially conforming in shape to a compressible, elastic, polymeric core member,
- b.) a lower end plate configured to attach to a lower spinous process with a second fixation structure comprising a pair of tabs configured such that, when the device is implanted, the lower spinous process lies between the pair of tabs containing openings for fixation to the lower spinous process, and further configured with a cavity situated opposite from the second fixation structure, the cavity substantially conforming in shape to the compressible, elastic, polymeric core member,
- c.) one or more flexible members selected from the group consisting of fibers, ribbons, and membranes extending between the upper end plate and the lower end plate and associating movement in one end plate with movement in the other end plate, and
- d.) said compressible, elastic, polymeric core member having a core axis along a core length, the core member having dimensions perpendicular to the core length that are all shorter than the core length, the core axis forming an included angle with the spinal axis greater than about 35° to and including 90° and further wherein the polymeric core member has a substantially circular core cross-section perpendicular to the core axis.

31. The device of claim 30 wherein the core member comprises elastomeric material.

32. The device of claim 30 wherein the core member comprises TPE.

33. The device of claim 30 wherein the core member is tapered.

34. The device of claim 30 wherein the core member is threaded.

35. The device of claim 30 wherein the upper end plate comprises the first fixation structure and an upper support member,
- wherein the upper support member contains the cavity substantially conforming in shape to the core member, and
- wherein the first fixation structure and the upper support member are removably slidably attachable to each other, and
- wherein the lower end plate comprises the second fixation structure and a lower support member,
- wherein the lower support member contains the cavity substantially conforming in shape to the core member, and
- wherein the second fixation structure and the lower support member are removably slidably attachable to each other.

36. The device of claim 35 wherein the first and second fixation structures comprise slidable keyways and wherein the upper and lower support members comprise members slidable within the slideable keyways.

37. The device of claim 35 wherein the one or more flexible members comprise more than one fiber interconnecting upper and lower end plates.

38. The device of claim 30 wherein the one or more flexible members comprise more than one ribbon interconnecting upper and lower end plates.

39. A spinal stabilization system comprising the interspinous process spinal stabilization device of claim 30 and an implantable prosthetic disc.

* * * * *